United States Patent
Luzbetak et al.

(10) Patent No.: US 11,642,441 B2
(45) Date of Patent: May 9, 2023

(54) SELF RETURNING CONTAMINATION BARRIER

(71) Applicant: Medela Holding AG, Baar (CH)

(72) Inventors: Mark A. Luzbetak, Kildeer, IL (US); Thomas A. Sutrina, Rockford, IL (US); Erich Pfenniger, Ebikon (CH); Patrik Bosshard, Buonas (CH)

(73) Assignee: MEDELA HOLDING AG, Baar (CH)

( * ) Notice: Subject to any disclaimer, the term of this patent is extended or adjusted under 35 U.S.C. 154(b) by 594 days.

(21) Appl. No.: 15/729,646

(22) Filed: Oct. 10, 2017

(65) Prior Publication Data

US 2018/0028731 A1     Feb. 1, 2018

Related U.S. Application Data

(62) Division of application No. 13/269,381, filed on Oct. 7, 2011, now Pat. No. 9,814,809, which is a division of application No. 11/591,276, filed on Nov. 1, 2006, now Pat. No. 8,187,227.

(51) Int. Cl.
*A61M 1/06* (2006.01)
*A61M 1/00* (2006.01)

(52) U.S. Cl.
CPC .............. *A61M 1/06* (2013.01); *A61M 1/062* (2014.02); *A61M 1/064* (2014.02); *A61M 1/78* (2021.05)

(58) Field of Classification Search
CPC .............. A61M 1/06; A61M 2001/064; A61M 2001/066; A61M 2001/068; A61M 2205/073
USPC ............... 604/74, 75, 537, 310, 323, 141
See application file for complete search history.

(56) References Cited

U.S. PATENT DOCUMENTS

| | | |
|---|---|---|
| 301,535 A | 7/1884 | Tatum |
| 316,584 A | 4/1885 | Turner |
| 1,670,610 A | 5/1928 | Colby |
| 2,148,918 A | 2/1939 | Weber |
| 2,273,679 A | 2/1942 | Westberg |
| 2,292,401 A | 8/1942 | Orre |

(Continued)

FOREIGN PATENT DOCUMENTS

| | | |
|---|---|---|
| AU | 2007318174 B2 | 7/2011 |
| CA | 2667089 C | 7/2012 |

(Continued)

OTHER PUBLICATIONS

International Search Report and Written Opinion for Int. App No. PCT/US2007/022507, dated Jun. 11, 2008.

(Continued)

*Primary Examiner* — Scott J Medway
(74) *Attorney, Agent, or Firm* — McDonnell Boehnen Hulbert & Berghoff LLP (57) ABSTRACT

A barrier of a vacuum pump prevents contamination from entering a vacuum pump air line. The barrier separates parts of the pump and is moveable between an initial state and a distended state. The barrier is assembled within the pump with a pre-load. When the vacuum source is applied to the barrier, the barrier achieves a distended state and when the vacuum source is released, the barrier incrementally self returns to an initial state. The geometry and material construction of the barrier, along with the pre-load, assists in returning the barrier on its own to the initial state from the distended state.

14 Claims, 9 Drawing Sheets

(56) References Cited

U.S. PATENT DOCUMENTS

| | | | |
|---|---|---|---|
| 2,371,632 A | 3/1945 | Lippincott |
| 2,419,795 A | 4/1947 | Saunders |
| 2,495,307 A | 1/1950 | Abramson |
| 2,687,845 A | 8/1954 | Young et al. |
| 3,083,943 A | 4/1963 | Steward, Jr. et al. |
| 3,140,085 A | 7/1964 | de Carbon |
| 3,465,112 A | 9/1969 | Reichert et al. |
| 684,078 A | 8/1972 | Nielsen |
| 3,738,363 A | 6/1973 | Lunas et al. |
| 784,780 A | 1/1974 | Laughlin |
| 3,782,385 A | 1/1974 | Loyd |
| 3,822,703 A | 7/1974 | Davisson |
| 3,830,238 A | 8/1974 | Kurtz et al. |
| 3,911,920 A | 10/1975 | Susinn |
| 3,931,834 A | 1/1976 | Caillet |
| D246,729 S | 12/1977 | Murphy |
| 4,249,481 A | 2/1981 | Adams |
| 4,263,912 A | 4/1981 | Adams |
| 4,323,067 A | 4/1982 | Adams |
| 4,411,603 A | 10/1983 | Kell |
| 4,427,470 A | 1/1984 | Kolff |
| 4,573,994 A | 3/1986 | Fischell et al. |
| 4,583,970 A | 4/1986 | Kirchner |
| 4,634,430 A | 1/1987 | Polaschegg |
| 4,649,863 A | 3/1987 | Hoefelmayr et al. |
| 4,673,388 A | 6/1987 | Schlensog et al. |
| 4,759,385 A | 7/1988 | Hudson, Jr. |
| 4,775,366 A | 10/1988 | Rosenblatt |
| 4,794,915 A | 1/1989 | Larsson |
| 4,799,922 A | 1/1989 | Beer et al. |
| 4,799,924 A | 1/1989 | Rosenblatt |
| 4,799,925 A | 1/1989 | Rosenblatt |
| 4,820,273 A | 4/1989 | Reinicke |
| 4,864,918 A | 9/1989 | Martin |
| 4,883,464 A | 11/1989 | Morifuki |
| 4,886,494 A | 12/1989 | Morifuji |
| 4,915,017 A | 4/1990 | Perlov |
| 4,961,726 A | 10/1990 | Richter |
| 5,009,638 A | 4/1991 | Riedweg et al. |
| 5,071,403 A | 12/1991 | Larsson |
| 5,089,020 A | 2/1992 | Koppert |
| 5,123,332 A | 6/1992 | Thayer et al. |
| 5,145,336 A | 9/1992 | Becker et al. |
| 5,149,413 A | 9/1992 | Maget |
| 5,242,406 A | 9/1993 | Gross et al. |
| 5,349,896 A | 9/1994 | Delaney, III et al. |
| 5,358,476 A | 10/1994 | Wilson |
| 5,749,850 A | 5/1998 | Williams et al. |
| 5,785,508 A | 7/1998 | Bolt |
| 5,814,019 A | 9/1998 | Steinbach et al. |
| 5,817,001 A | 10/1998 | Leschinsky et al. |
| 5,941,847 A | 8/1999 | Huber et al. |
| 6,110,140 A | 8/2000 | Silver |
| 6,378,739 B1 | 4/2002 | Maas et al. |
| 6,390,338 B1 | 5/2002 | Baudin |
| 6,461,324 B1 | 10/2002 | Schlensog |
| 6,499,729 B1 | 12/2002 | Walterbusch |
| 6,530,900 B1 | 3/2003 | Daily et al. |
| 6,547,756 B1 | 4/2003 | Greter et al. |
| 6,652,510 B2 | 11/2003 | Lord et al. |
| D484,236 S | 12/2003 | Renz et al. |
| 6,663,587 B2 | 12/2003 | Silver et al. |
| D485,614 S | 1/2004 | Renz et al. |
| D486,223 S | 2/2004 | Robson et al. |
| 6,699,213 B1 | 3/2004 | Annis et al. |
| 6,706,012 B2 | 3/2004 | McKendry et al. |
| 6,729,494 B2 | 5/2004 | Portman et al. |
| 6,746,637 B1 | 6/2004 | Huss et al. |
| 6,749,582 B2 | 6/2004 | Britto et al. |
| 6,776,591 B1 | 8/2004 | Rinninger et al. |
| 6,863,648 B2 | 3/2005 | Williams et al. |
| 6,994,030 B2 | 2/2006 | Perut et al. |
| 7,029,454 B2 | 4/2006 | Watanabe |
| 7,066,874 B2 | 6/2006 | Riebman et al. |
| D609,330 S | 2/2010 | Paterson et al. |
| D609,331 S | 2/2010 | Paterson et al. |
| 7,727,182 B2* | 6/2010 | Silver ............ A61M 1/06 604/74 |
| 7,806,855 B2 | 10/2010 | Kliegman et al. |
| 8,187,227 B2 | 5/2012 | Luzbetak et al. |
| D676,956 S | 2/2013 | Kirchner |
| 8,915,880 B2* | 12/2014 | Darnell ............ A61M 1/06 604/74 |
| 9,011,372 B2 | 4/2015 | Jones |
| D773,643 S | 12/2016 | Luzbetak et al. |
| 9,814,809 B2 | 11/2017 | Luzbetak et al. |
| 2003/0004459 A1 | 1/2003 | McKendry et al. |
| 2003/0050623 A1 | 3/2003 | Lord et al. |
| 2003/0139702 A1 | 7/2003 | Renz et al. |
| 2003/0149398 A1 | 8/2003 | Renz et al. |
| 2004/0087898 A1 | 5/2004 | Weniger |
| 2004/0158199 A1 | 8/2004 | McKendry et al. |
| 2005/0154348 A1 | 7/2005 | Lantz et al. |
| 2005/0154349 A1 | 7/2005 | Renz et al. |
| 2005/0228342 A1 | 10/2005 | Yuen |
| 2006/0111664 A1* | 5/2006 | Samson ............ A61M 1/064 604/74 |
| 2008/0009815 A1 | 1/2008 | Grabenkort et al. |
| 2008/0033352 A1 | 2/2008 | Annis et al. |
| 2008/0171970 A1 | 7/2008 | Luzbetak et al. |
| 2008/0208115 A1 | 8/2008 | Kliegman et al. |
| 2009/0099511 A1 | 4/2009 | Sutrina et al. |
| 2010/0174232 A1* | 7/2010 | Wortley ............ H01L 33/58 604/74 |
| 2010/0228188 A1 | 9/2010 | Kunzler et al. |
| 2010/0324477 A1 | 12/2010 | Paterson et al. |
| 2010/0324478 A1 | 12/2010 | Kazazoglu et al. |
| 2011/0245763 A1 | 10/2011 | Myers |
| 2013/0023821 A1 | 1/2013 | Khalil et al. |
| 2015/0314053 A1 | 11/2015 | Furrer et al. |
| 2015/0328380 A1 | 11/2015 | Furrer et al. |

FOREIGN PATENT DOCUMENTS

| | | |
|---|---|---|
| CN | 2580971 Y | 10/2003 |
| CN | 101553264 A | 10/2009 |
| DE | 2658322 A1 | 6/1978 |
| DE | 8714995 U1 | 12/1987 |
| EP | 0466462 A1 | 1/1992 |
| EP | 2077868 B1 | 7/2016 |
| FR | 1067421 A | 6/1954 |
| GB | 185521 A | 9/1922 |
| GB | 759051 A | 10/1956 |
| GB | 2082920 A | 3/1982 |
| JP | 2002-035111 A | 2/2002 |
| JP | 2004-000486 A | 1/2004 |
| JP | 2006-015004 A | 1/2006 |
| JP | 5121840 B2 | 1/2013 |
| KR | 10-1193891 B1 | 10/2012 |
| MX | 2009004790 A | 5/2009 |
| WO | 2004/058330 A1 | 7/2004 |
| WO | 2006/052485 A2 | 5/2006 |
| WO | 2008/057218 A2 | 5/2008 |

OTHER PUBLICATIONS

Spectra Spare Parts/Accessories—Backflow Protector Membranes (2 pk). Pupsik. posted as early as Feb. 17, 2014 online. www.pupsikstudio.com. Date accessed Apr. 13, 2016. <http://www.pupsikstudio.com/spectra-spare-parts-accessories-large-membrane-s1-s2-m1-2-pk.html>.

Medela Swing and Swing Maxi. Best Breast Pump Reviews, www.bestbreastpumpreviewsformoms.com. Date accessed Apr. 13, 2016. <http://www.bestbreastpumpreviewsformoms.com/medela-swing-and-swing-maxi/>.

* cited by examiner

SELF RETURNING CONTAMINATION BARRIER

CROSS-REFERENCE TO RELATED APPLICATIONS

This application is a divisional application of U.S. patent application Ser. No. 13/269,381, filed Oct. 7, 2011, which is a divisional application of U.S. patent application Ser. No. 11/591,276, entitled "Self Returning Contamination Barrier," filed Nov. 1, 2006, that issued as U.S. Pat. No. 8,187,227 on May 29, 2012, the contents of which are fully incorporated herein by reference.

FIELD OF THE INVENTION

The present invention relates generally to contamination barriers for pumps, and more particularly in one aspect to a breastpump assembly including an improved barrier to prevent milk from entering and possibly contaminating a pumping mechanism for the breastpump.

BACKGROUND OF THE INVENTION

Breastpumps are well known, and generally comprise a hood or shield that fits over the breast, a vacuum pump connected to the hood for generating an intermittent vacuum (or negative pressure) within the breastshield, and a receptacle for expressed milk. Negative pressure is pressure below atmospheric pressure. The intermittent suction action of the vacuum pump serves to pull on the breast and nipple and thereby express milk. The expressed milk typically flows from the hood, through a conduit structure and into a collection container, such as a baby bottle, for storage and later use.

Breastpumps can be manually or electrically operated. With manually operated pumps, the pumping action is done by reciprocating a piston or lever by hand, or compressing a flexible bulb, as shown in Medela's U.S. Publication No. 2004/0039330. With electrically operated pumps, the pumping action generated by a motor driven pump and typically conveyed by an air hose, or air line, that connects to the breastshield assembly.

In most instances, the pressure applied at the breast is a negative pressure (suction). That negative pressure is typically applied to the interior of the breastshield in a singular fashion, that is, without any kind of differential vacuum application over the breastshield as a whole. This has ordinarily been done through a cyclic pattern, e.g., intermittent suction. Breastpumps of this kind, which only pull and release suction, are known as simple pumps.

There are also breastpumps that apply a vacuum pressure and a positive pressure, typically applied to the interior of the breastshield, known as complex pumps. Typically, a vacuum pump that generates a positive pressure, (pressure above atmospheric pressure,) assists in forcing the expressed milk through a valve and into the collection container. A breastpump of the foregoing type is shown in U.S. Pat. No. 4,857,051 to Larsson, the disclosure of which is incorporated herein by reference for further details of a breastpump assembly in general.

Positive pressure opens the valve, often used with breastpumps, to assist in movement of the breast milk through the conduit structure and into the bottle. During pumping, the expelled milk will ultimately be separated from the air drawn back and forth in the air hose, and to and from the breastshield. Some breastpumps use gravity and geometry, such as a splashguard, to separate the milk and air (air being the working fluid), but these breastpumps are often difficult to clean, and the orientation of the breastshield in use may be thereby limited. Other breastpumps use a filter, for example a hydrophobic filter, to prevent milk from entering the air hose and/or pump. That filter can become saturated, shutting down pumping; it must also be cleaned and even periodically replaced. The objective of these efforts is to isolate parts of the breastpump from milk or other liquids/bacteriological material that would constitute a contaminant, or foul the works (such as milk finding its way to the pump mechanism). In institutional settings, for another example, it is desirable to have a pump that can be transferred between mothers, yet the pump mechanism remains isolated from one mother to the next.

Some conventional electric breastpumps also use a moveable, sometimes collapsible, membrane or barrier, that separates the breastshield (including valve) from the pumping mechanism. During operation, two pressures are realized: a first pressure on the vacuum side of the membrane, or pump vacuum, and a second pressure on the breastshield side of the membrane, or breastshield vacuum. The vacuum pump communicates a negative pressure to the membrane via the air hose, such that the first pressure is greater than the second pressure, or in similar terms, the pump vacuum is greater than the breastshield vacuum. This differential vacuum causes the membrane to collapse or move. A problem with some conventional breastpumps of this type is that the membrane may not return to an initial state or position, i.e., it may end up locking or buckling.

This type of breastpump generally requires a positive pressure from the breastshield side of the membrane to push the membrane past a lock or buckle point in order to return the membrane to the non-collapsed state during a breastpump cycle. A breastpump of the foregoing type is shown in U.S. Pat. No. 5,941,847 to Huber. A typical issue with these types of pumps is that leakages, evaporation, expulsion of milk and breast extension hysteresis do not ensure that the membrane returns fully to its initial non-collapsed state without the assistance of a positive pressure.

Some conventional manual breastpumps also include a collapsible or movable membrane that has a significant energy loss in "transferring" vacuum from one side to the other. The mechanical coefficient across the barrier membrane needs dramatic improvement.

Accordingly, a breastpump that reduces or eliminates contamination in the upstream pump air line and pump by isolating the pressure source from the expressed milk is desired to protect the user and prevent damage to the pump mechanism. A much more energy efficient pump system that uses a movable membrane/barrier for vacuum communication is also highly desirable.

SUMMARY OF THE INVENTION

The present invention, in perhaps one of its broadest expressions, comprises a barrier for a pump or a pumping system, that separates parts of the pump while transferring a pressure change across the barrier. When a pressure, as from a vacuum source, is applied to the barrier, the barrier achieves a distended state and when the vacuum is released, as by a return to atmospheric pressure, the barrier has a natural bias that returns it to an initial "pre-loaded" state. This advantageously can actually yield a slight positive pressure from the system and the breastshield side or the downstream side of the barrier (relative to the upstream vacuum source). "Bias" is used herein to describe the pre-set tendency of the barrier to try and return to this initial state.

Although embodiments of the present invention discussed herein are directed to breastpump systems, it is contemplated that various other applications for a self-returning barrier exist, for example, in a general sense to similar pump systems. This applies to other attributes of the invention as well.

Another object of the present invention is to provide a self-returning barrier such that a source of positive pressure from the pump is not required to return the barrier to its initial state from a distended state during a breastpump cycle, and further that the mechanical transfer of vacuum across the barrier is highly efficient. The force required to distend the barrier of the present invention is determined by material construction, breastshield size, breast size, and the vacuum level of the pump; but in any of these systems, displacement of the barrier to a distended state requires that the pump vacuum is greater than the breastshield vacuum, i.e., there is energy lost in the mechanical transfer of vacuum from one side of the barrier to the other. The present invention achieves a highly efficient mechanical transfer.

The geometry of the inventive barrier acts as a spring in a preferred form. The barrier geometry maintains a low spring rate. A sufficient spring force designed into the barrier returns the barrier to the initial state, and further can assist in the expulsion of milk through a valve and into a collection container.

Another object of the present invention is to provide a barrier with a pre-loaded residual force when assembled. That is, the barrier is compressed along a central axis in the assembled state. The barrier is thus pre-loaded, i.e., biased when in this assembled state.

Yet another object is to provide a self-returning barrier that returns to an initial state from a distended state in a brief time frame, i.e., 150 milliseconds or less, without assistance from the pump to thereby further, minimize energy expenditure on the breastpump system.

Another object of the present invention is to provide a barrier to isolate parts of the pump, as from contaminants or the like that could otherwise pass.

Yet another aspect of the present invention is to provide a self-returning barrier that collapses uniformly as well as returns to an initial state uniformly. The barrier of the present invention thereby eliminates the need to apply force to move through non-uniform states, such as in a lock or buckle condition of the prior art. The barrier of the present invention includes a corrugated geometry to prevent it from locking up or buckling. In one form this geometry comprises one or more undulations in the barrier that are generally concentric on a convex surface.

During collapse or achievement of a distended state, the barrier of the present invention in a preferred form never locks or buckles, even during circumstances when the pump vacuum remains less than the breastshield vacuum or when the pump vacuum is equal to the breastshield vacuum. Likewise, the barrier of the present invention never locks or buckles during return from a distended state to an initial state, even during the circumstances when the vacuum pressure is greater than the breastshield vacuum or the vacuums are equal.

Another aspect of the present invention is to provide a self-returning barrier that works with manually operated as well as electrically operated breastpumps. Furthermore, a self-returning barrier is provided that may function with complex electrical pumps providing a negative pressure and a positive pressure, and also with a simple pump providing only negative pressure (and a vent to atmosphere).

In particular, the barrier of the present invention does not require assistance from the vacuum pump, such as the positive force of air, for the barrier to return to its initial state during a breastpump cycle. The geometric and material construction of the barrier itself returns the barrier to its initial state after a suction phase.

In a broad embodiment, the present invention is a movable barrier for separating parts of a pump, as to prevent contamination that includes an initial state wherein the barrier is assembled as to possess a pre-load. When a vacuum source is applied to the barrier, the barrier achieves a distended state, and when the vacuum source is released, the barrier incrementally self-returns to an initial state.

The present invention, with application to a breastpump assembly, has a breastshield, a conduit structure and a collection container (bottle). A resilient barrier is assembled in a pre-loaded condition in a housing, which is located in an air pressure line, typically a vacuum line. When a vacuum is applied, the barrier achieves a distended state, and when the vacuum is released, the barrier utilizes the pre-load as a spring action to assist in transforming to its initial pre-load state.

In another aspect, a breastpump assembly has a contamination barrier located in a vacuum line between a vacuum pump and a breastshield. A housing has a breastshield side and a vacuum side, also referred to herein as vacuum pump side, separated and isolated from one another by the barrier. The barrier is assembled within the housing in an initial pre-loaded state such that said barrier has a bias toward the breastshield side when no vacuum is applied. When vacuum is applied, the barrier achieves a distended state, and when the vacuum is released, the barrier returns to the initial state.

In one embodiment, the barrier has a generally convex shape at least in part as presented by a convex barrier side, and is assembled within the foregoing housing so that the bias presses the convex barrier side against an internal breastshield side sidewall of the housing in the initial state. The convex barrier side has at least one undulation formed in its surface generally concentric with the center of the convexity of the barrier. In a most preferred form, the internal breastshield side sidewall has a shape that generally conforms to that of the convex barrier side, such that the barrier and the breastshield side sidewall substantially mate when in facial engagement (in the initial pre-load state or condition).

In the foregoing embodiment, the barrier becomes inverted under vacuum, and forms another generally convex shape when distended under vacuum, at least in part, as presented by the now inside-out barrier side in the distended state. A vacuum side sidewall has in this most preferred form, a shape that generally conforms to that of the distended barrier side, such that the barrier and the vacuum side sidewall substantially mate when in facial engagement.

In another aspect of the present invention, the barrier has a plurality of generally concentric undulations designed to provide bending moments for the barrier tending to return from a distended state to an initial state. This is contrasted with stretching of a barrier of the prior art, rather than bending.

It is yet another advantage of the present invention to provide a breastpump assembly which isolates parts of the pump in a vacuum line from contamination, such as between a breastshield and a vacuum source in communication with the breastshield via the vacuum line. The vacuum line is in communication with a housing that has a breastshield side and vacuum side. A resilient barrier having a form with a first surface that is, at least in part, generally domelike with an unassembled dome height as measured from a base of the dome to the first surface. The resilient barrier is assembled in the housing in a manner to separate and thereby isolate the breastshield housing side and vacuum housing side in an initial state with a pre-loaded condition for the barrier. The pre-loaded condition of the barrier has an assembled dome height that is less than the unassembled dome height.

Furthermore, the vacuum realized on the breastshield side follows a generally one to one relationship with the vacuum applied on the vacuum side, after an initial level of vacuum is realized on the vacuum pump side to overcome the pre-load condition. The initial level of vacuum to overcome the pre-load condition can be about 4 to 15 mmHg (negative) in one form of the invention. This yields a highly efficient vacuum transfer across the barrier. The foregoing embodiment can further include a milk conduit structure which conveys milk from the breastshield to a container via a catch chamber and a one-way valve between the catch chamber and the container. The barrier, upon returning to an initial state with a predetermined minimum amount of milk in the catch chamber, generates an increased pressure in the catch chamber relative to the container so as to open the valve and release milk to travel into the container.

These, together with other objects and advantages will be further understood in the details of the construction and operation of the invention as more fully hereinafter described, reference being had to the accompanying drawings, forming a part hereof, wherein like numerals refer to like parts throughout, in which:

DETAILED DESCRIPTION OF AN EMBODIMENT OF THE INVENTION

Although the embodiments of the present invention described herein are directed to breastpump assembly systems, which is the particular environment that the invention finds its origin, it is contemplated that the present invention has various other applications, such as any pump system that requires a barrier to prevent contamination, or that may benefit from a movable membrane that is very efficient in transmitting pressure changes from a volume (or working fluid) on one side to a volume (or working fluid) on the other side.

The barrier of the present invention works with simple manually operated breastpumps that may provide only suction (and a vent to atmosphere), as well as more complex pumps, such as motorized pumps, and pumps providing both suction and a positive pressure. Thus, while described in particular respects with a source of vacuum, the pressure source could also be a positive pressure moving the barrier.

Figure 1A:
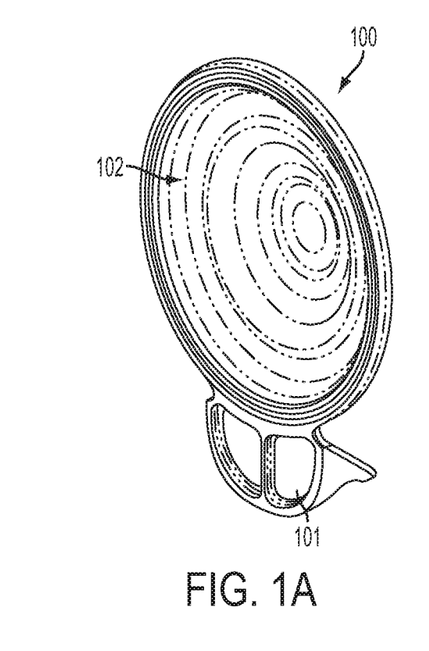
FIG. 1A is a perspective view of a contamination barrier in a free state according to the present invention.
Figure 1B:
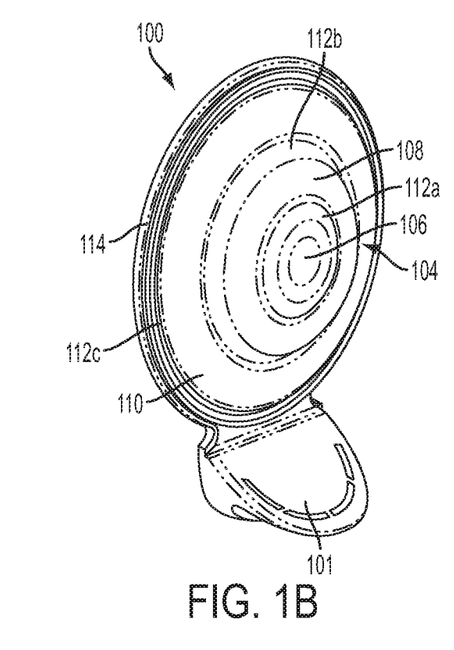
FIG. 1B is a perspective view of the barrier of FIG. 1A from the other side.

FIGS. 1A and 1B illustrate a self-returning contamination barrier 100 in a "free" state according to the present invention; that is, unassembled, and as it may be molded. The barrier includes an inner surface 102, and outer surface 104. As shown, the outer surface 104 includes three concentric circular panels 106, 108, 110, although any number of panels and any concentric shape are contemplated. The panels 106, 108, 110 are amalgamated, or joined, via sidewalls 112. Sidewall 112a joins center panel 106 to intermediate panel 108. Sidewall 112b joins intermediate panel 108 to exterior panel 110. Exterior panel 110 is amalgamated (joined) with a rim 114 via sidewall 112c. As shown, and discussed in more detail hereafter, a valve 101 formed integral with barrier 100, but it is contemplated that the valve 101 could be separate and apart from the barrier 100.

The self-returning contamination barrier 100 is made of a resilient material, such as an elastomer, or any plastic and rubber combination that permits the barrier to function as a spring, described more fully below. The preferred embodiment is constructed of liquid injection molded silicone (LIMS), such as LIM 6050 that available from General Electric (GE).

Figure 3A:
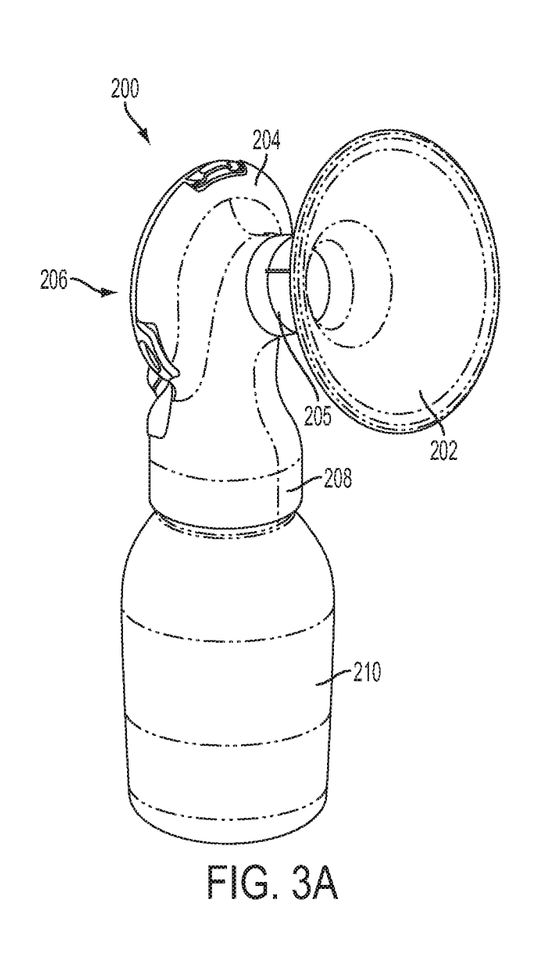
FIG. 3A is a front side perspective view of a breastpump assembly according to the present invention.
Figure 3B:
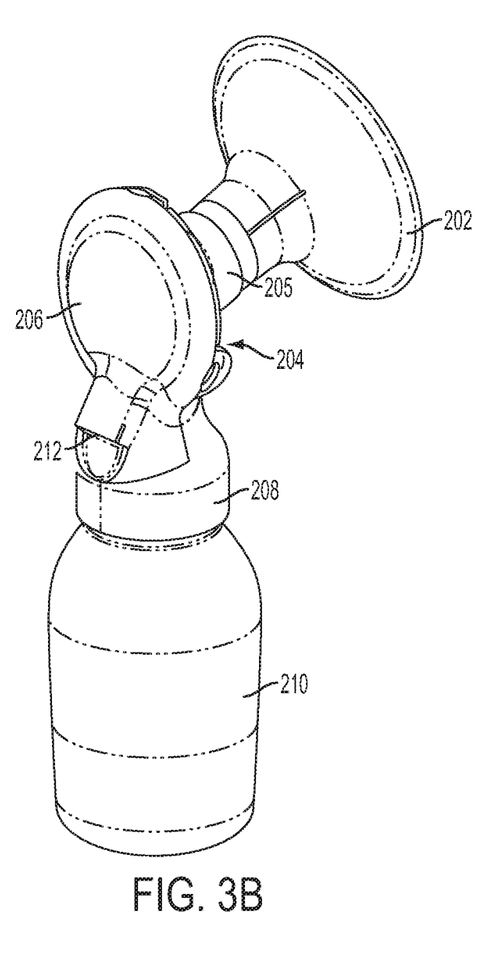
FIG. 3B is the breastpump of FIG. 3A from the back side.

The barrier 100 is assembled with a breastpump protection to eliminate contamination in the pump air line. FIGS. 3A and 3B illustrate a breastpump assembly 200. The assembly 200 includes a detachable breastshield 202. The breastshield 202 engages with a breast to form a seal to ensure suction to the breast, while maintaining comfortability. The front housing 204, also referred to herein as first housing, front side, or breastshield side, includes an interface or base part 205 and bottle collar 208. Breastshield 202 is detachably connected to the interface 205 of front housing 204 (although it could be made integral therewith). A collection container or bottle 210 is attached to the collar 208 of the front housing 204. The rear housing 206, also referred to herein as second housing, back side, or vacuum side, includes a port 212 to connect to an electrically operated pump, otherwise referred to as the vacuum source.

Figure 4:
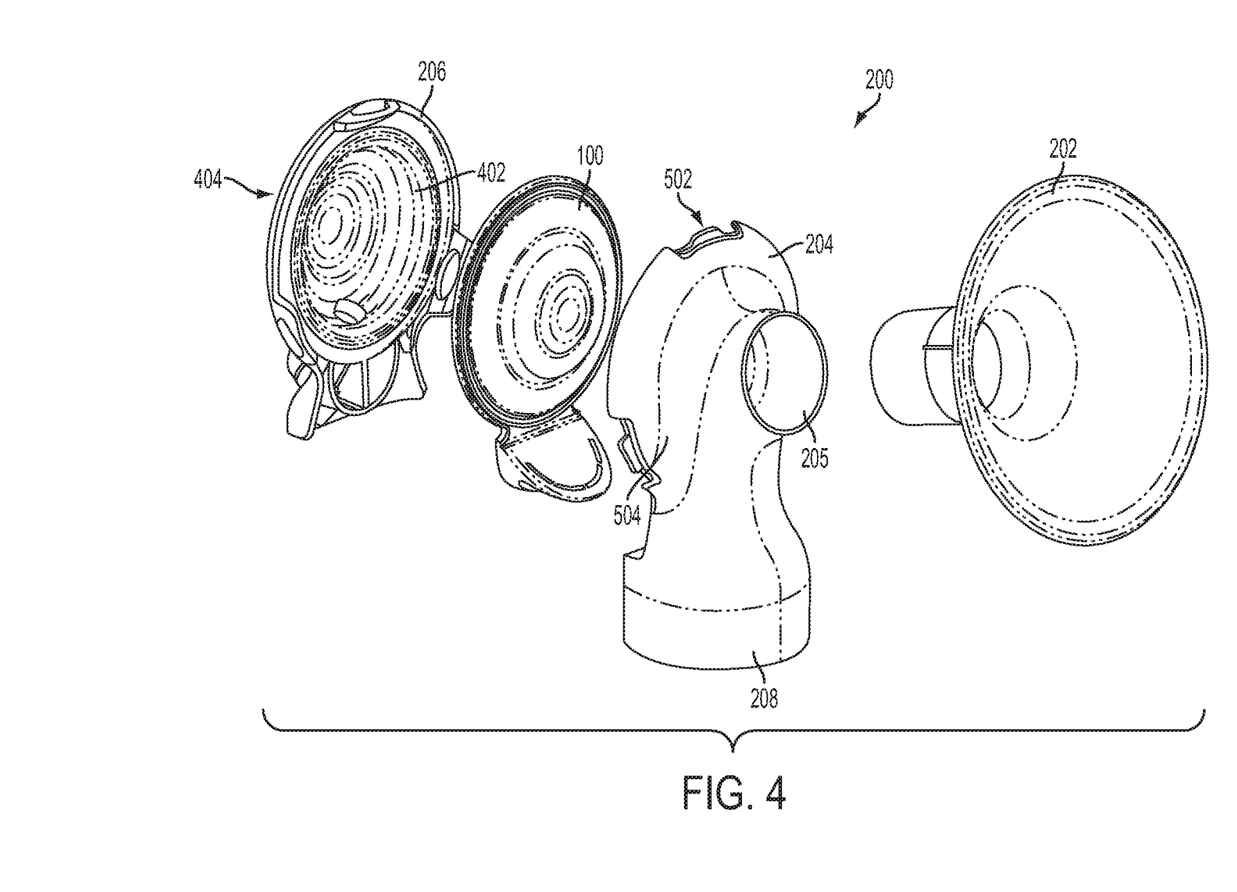
FIG. 4 is an exploded perspective view from the front side of the breastpump assembly of FIGS. 3A and 3B according to the present invention (without the bottle)
Figure 5:
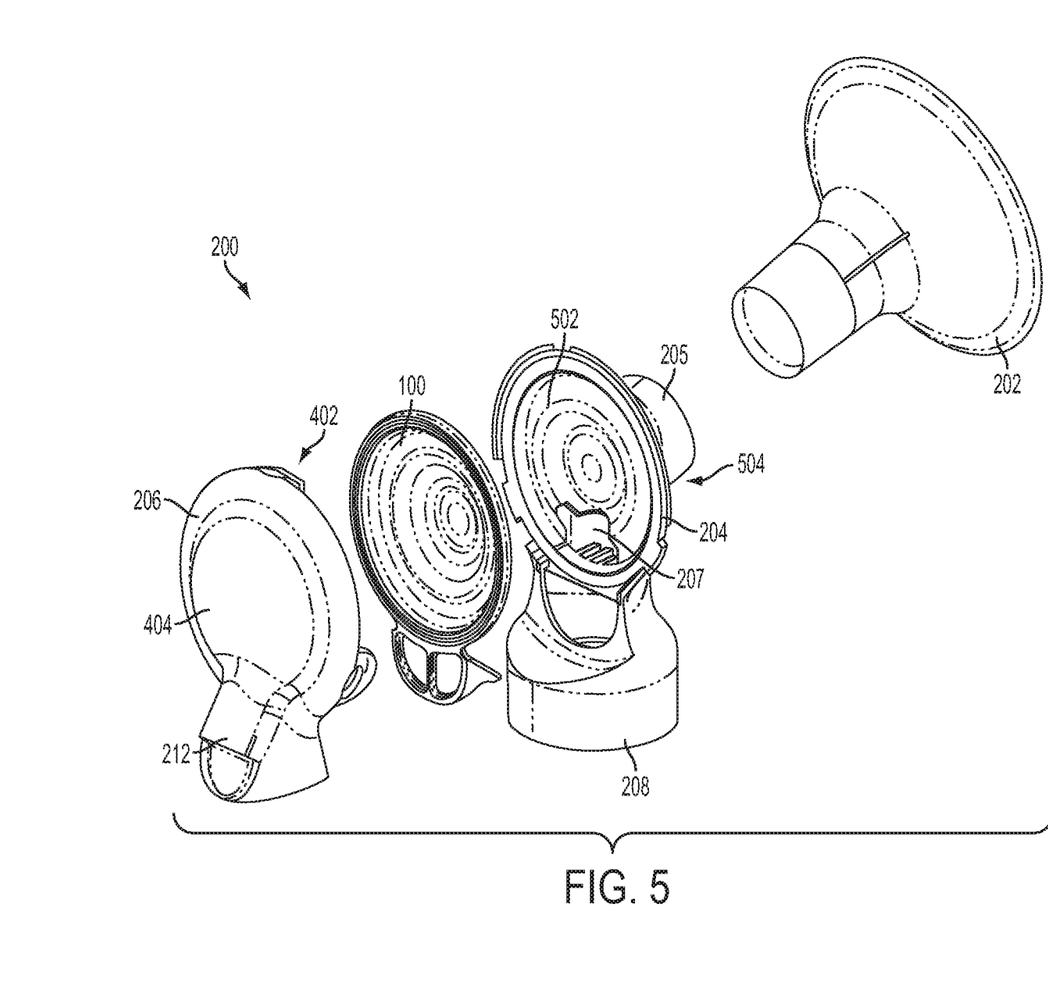
FIG. 5 is an exploded perspective view from the back side of the breastpump assembly of FIG. 4.

FIG. 4 and FIG. 5 illustrate an exploded view of the breastpump assembly 200 according to the present invention. The rear housing 206 includes an interior rearwall surface 402 and an exterior surface 404. The front housing 204 includes an interior frontwall surface 502, and an exterior surface 504. As assembled, the barrier 100 is positioned between the interior rearwall surface 402 of the rear housing 206 and the interior frontwall surface 502 of the front housing 204.

The frontwall surface 502 most preferably has a shape that generally matches the outer surface 104 of the barrier 100 when it is in facial engagement in the initial state. The interior rearwall surface 402 most preferably has a shape that generally matches the inner surface 102 of the barrier 100 in a distended (inverted) state, described more fully below. The rim 114 forms a seal between the interior surface 502 of the front housing part 204 and the interior surface 402 of the rear housing part 206.

Figure 6A:
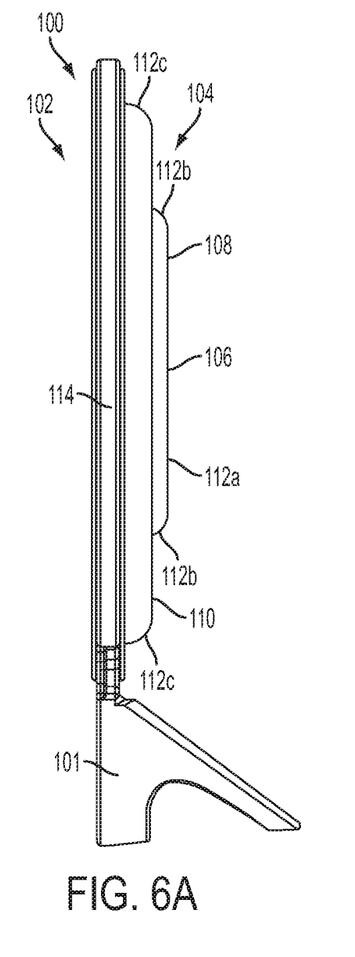
FIG. 6A is a side view of the contamination barrier of FIG. 2 in a pre-loaded state according to the present invention.

Once assembled within the housing, the barrier 100 separates and isolates the breastshield side of the housing 204 and the vacuum side of the housing 206. The barrier 100 is assembled in a pre-loaded initial state, also referred to herein as a first or initial position, or state, and maintains a concave shape as viewed from the vacuum side or a convex shape as viewed form the breastshield side, between the housing parts 204, 206, as shown in FIG. 6A. In this first position, the barrier 100 is biased toward the breastshield side of the housing 204.

Figure 2:
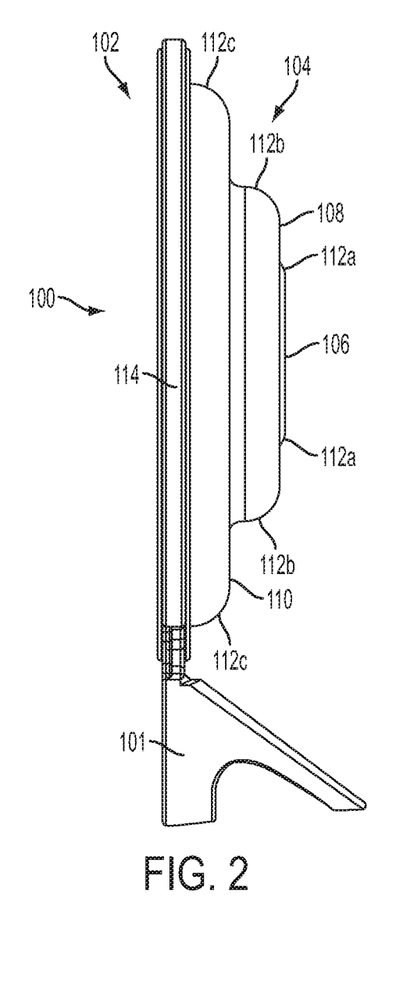
FIG. 2 is a side view of the contamination barrier of FIG. 1.

As can be seen from FIG. 6A, the center panel 106 and sidewall 112a are substantially aligned with intermediate panel 108 in the pre-loaded state, i.e., when assembled. In addition, sidewalls 112b, 112c in a compressed configuration in the pre-loaded state, in comparison to the free state (FIG. 2). Looking at this another way, the barrier 100 has a dome-like shape, with a central axis. In the free state of FIG. 2, the height of the dome, as taken along this axis from rim 114 to the front surface of the convex side (panel 106), is $h_1$. In the pre-load state of FIG. 6A, the dome is compressed to a height of $h_2$, where $h_2$ is less than $h_1$. The pre-loaded state assists in the functionality (spring action) of the barrier 100 during operation, described more fully below.

Figure 7A:
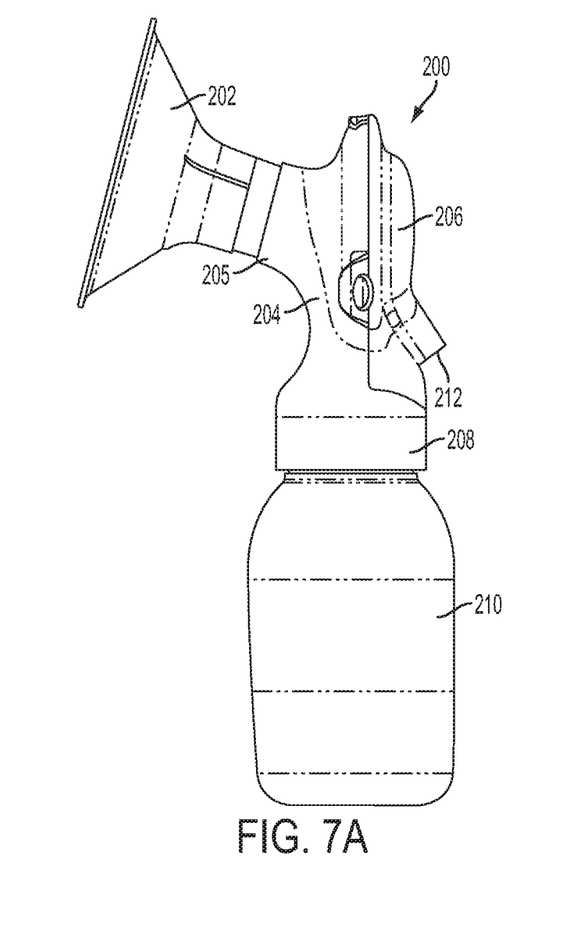
FIG. 7A is a side sectional view of the breastpump assembly of FIGS. 3A and 3B.
Figure 7B:
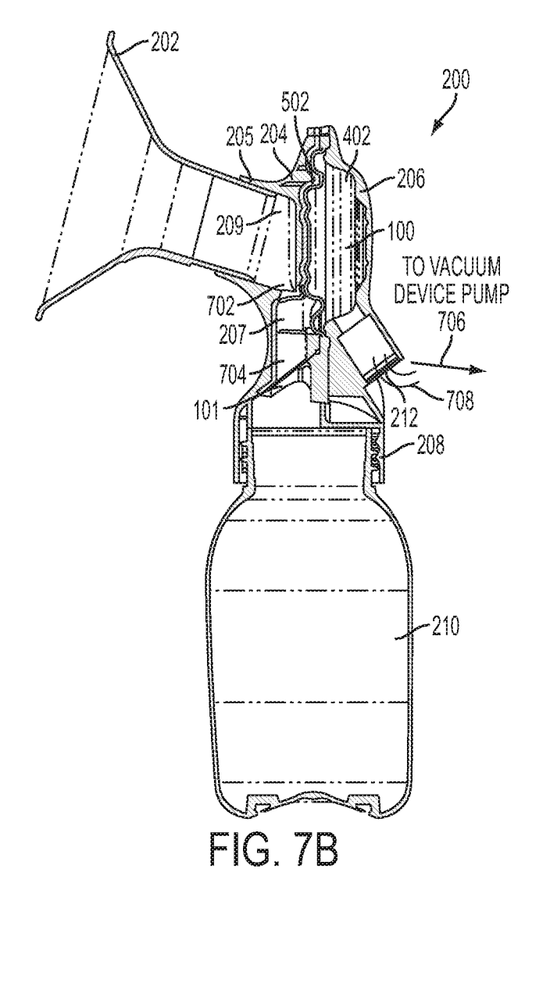
FIG. 7B is a sectional view of the breastpump assembly of FIG. 7A.

With reference to FIGS. 7A and 7B, the breastshield 202 connects to the interface (collar or shield base) 205 of the front housing 204. When milk is expressed from the breast of a nursing mother, the milk thereby flows from the breastshield 202 through a liquid conduit 702 portion to a collecting or catch chamber 704, and then to the collection container 210 (here, a bottle). At the outlet of the collection chamber 704 there is provided a valve 101 which closes the collection chamber 704, leading to bottle 210. Valve 101 in this instance is shown integrated with barrier 100, but again, it is contemplated that the valve 101 could be separate and apart from the barrier 100. This system is not dependent on this type of valve, in any event.

When a vacuum or negative pressure is applied to the breastshield 202 from a well known type of suction device 706, which may be manually operated or motor driven, the valve 101 closes the collection chamber 704, and a negative pressure is applied to the interior of the breastshield 202. Milk is collected within the collection chamber 704. When the negative pressure is released, the valve 101 opens to pass milk expressed into the breastshield 202 and thence to the collection chamber 704, to flow into the bottle 210. As noted, the valve mechanism may be of many types, for example a duckbill type.

The vacuum or suction device 706 here is a house-current driven vacuum pump using a tube, or air line 708 to convey the vacuum, although it is contemplated that the vacuum device 706 may be a manually operated piston pump, or a battery operated diaphragm pump. The invention herein is, however, not limited to any particular kind of vacuum device.

The vacuum source 706 connects via air line tube 708 to a port 212 formed on the rear housing 206. The port 212 extends through surface 402 and communicates with the interior of the rear housing 206. There is an interior surface 502 of the front housing 204, against which the barrier 100 is initially positioned, as shown in FIG. 7B. The breastshield side of the housing 204 has an aperture 207 that extends into the conduit structure communicating with interior space 209 within the connecting collar 208. The vacuum in the rear housing 206 is thereby communicated to the breastshield 202 by movement of the barrier away from the front wall surface 502, which in turn draws air through aperture 207 from space 209 and within the breastshield 202. The above describes a vacuum conduit structure which conveys the vacuum from the source 706 to the breastshield 202.

As stated, just before the vacuum source is applied, the barrier 100 is in facial engagement with the interior front-wall surface 502 of the front housing 204. The frontwall surface 502 has a shape that generally matches the outer surface 104 of the barrier 100 in this initial state. This matching engagement, which could also be less exact for substantially matching engagement, provides the smallest amount of "dead" volume on the breastshield side. It should be appreciated that the invention provides a very efficient vacuum transfer mechanism, which will use less energy and therefore extend the useful life of a battery-operated pump.

Figure 8:
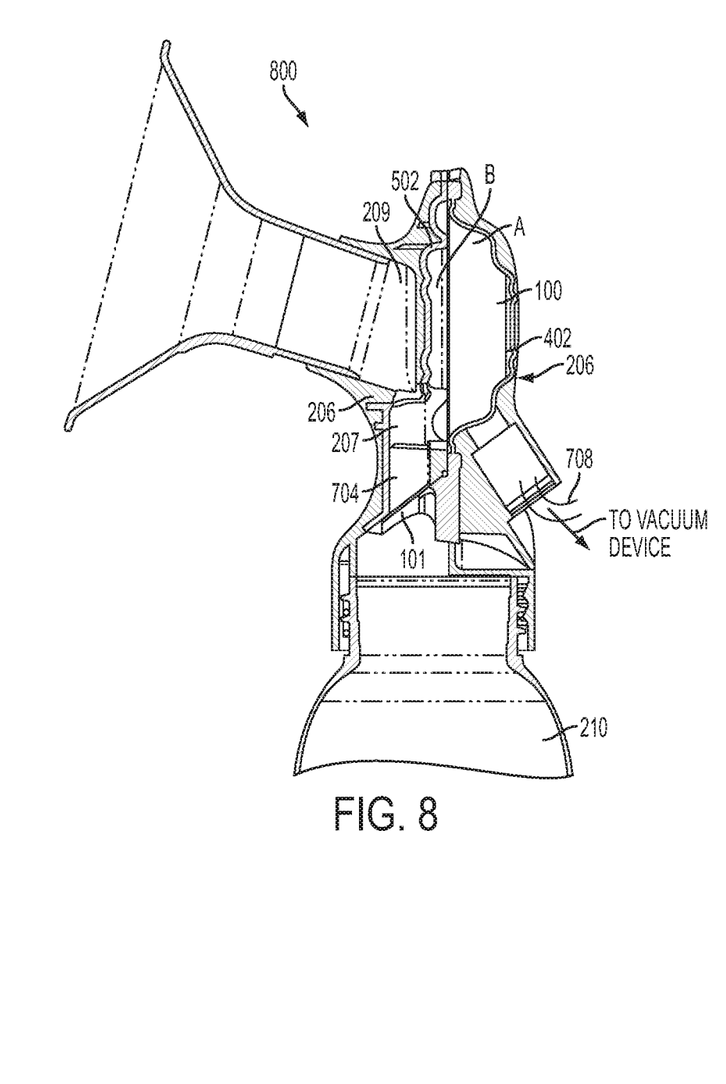
FIG. 8 is an enlarged sectional view similar to that of FIG. 7B in one phase.
Figure 9:
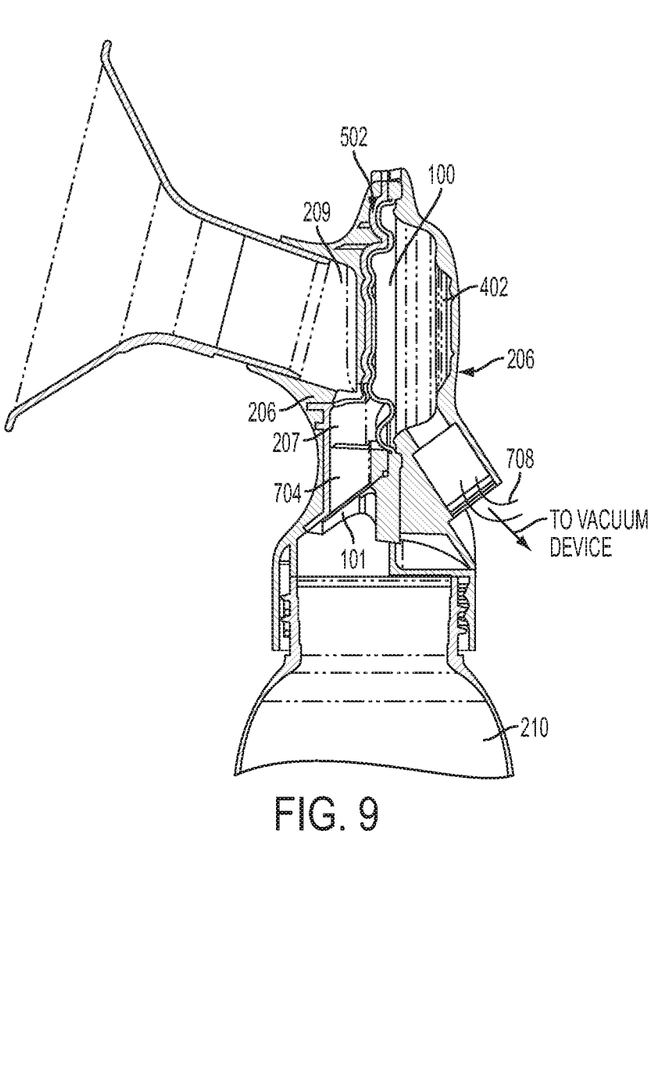
FIG. 9 is a sectional view similar to that of FIG. 8 in another phase.

The breastpump assembly 200 of the present invention operates through a breastpump cycle of suction, air line release, and milk release. FIGS. 8 and 9 illustrate the breastpump in the first phase, or suction phase. During operation, two pressures are realized on each side (breast-shield side and vacuum side) of the barrier 100: a first pressure A on the vacuum side of the barrier 100, otherwise referred to herein as pump vacuum, and a second pressure B on the breastshield side of the barrier 100, otherwise referred to herein as breastshield vacuum. The pump 706 communicates a negative pressure to the barrier 100 via the air line 708 such that the first pressure A is at least initially greater (more negative) than the second pressure B, yielding what is known as a differential vacuum. This differential vacuum ultimately causes the barrier 100 to reach a distended state. The pump 706 draws a negative pressure (relative to atmosphere), which pulls the barrier 100 back into a second position, or distended state (see FIG. 8). The now inverted barrier 100 is in facial engagement with interior rearwall surface 402 of the rear housing 206 in the full distended state. The rearwall surface 402 has a shape that generally matches the inner surface 102 of the barrier 100 in this distended state.

Figure 6B:
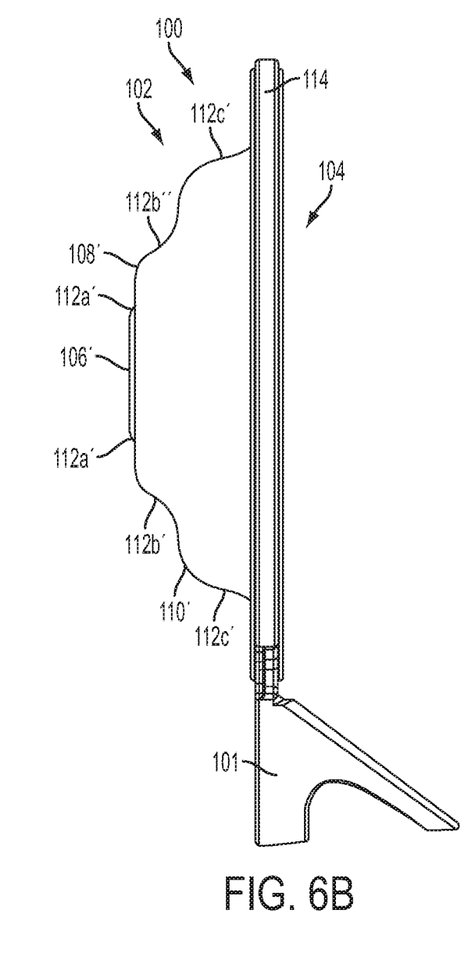
FIG. 6B is a side view similar to that of FIG. 6A with the barrier distended.

As shown in FIG. 6B, when a vacuum is applied to the inner surface 102 of the barrier 100, the barrier 100 essentially turns inside out, such that an initial convex shape (FIGS. 2 and 6A) is transformed to an inverted convex shape (FIG. 6B). The center panel 106' is displaced from intermediate panel 108' via sidewall 112a', while the intermediate panel 108' is displaced from the exterior panel 110' via 112b' and the exterior panel 110' is displaced from the rim 114 via sidewall 112c'. Sidewalls 112a', 112b', 112c' are substantially lengthened in the distended state 900 in comparison to both the free state (FIG. 2) and the initial state (FIG. 6A).

As the barrier transforms to and from a distended state and an initial state, the exact position of barrier between the front housing 204 and rear housing 206 is determined by the difference between the first pressure A on the vacuum side of the barrier and the second pressure B on the breastshield side, i.e., differential vacuum. In addition to a first pressure and second pressure, the barrier 100 defines a first volume on the vacuum side and a second volume on the breastshield side. It should be noted that as the barrier moves, the first volume and second volume (in addition to the first pressure and second pressure) change respectively.

In the collection chamber release phase, vacuum is released, typically by release to atmospheric pressure into the air line 708. The breastpump enters the air line release phase where energy stored (pre-load) in the barrier 100 causes the barrier 100 to return to its initial state (FIGS. 6A and 9). The second pressure B returns to atmospheric level if no milk has been added to the collection chamber 704. If no milk, or air from leakage around the breast, has been added to the collection chamber 704, the valve 101 does not open and the breastpump cycle repeats until milk is collected in the collection chamber 704. If milk is present, however, the air volume in the breastshield side will have been reduced by the milk volume. The barrier 100 pre-load then creates an overpressure (relative to the container) within the collection chamber 704, opening the valve 101. That is, as the barrier 100 transforms from the distended state, the differential vacuum reverses wherein the first pressure A decreases and the second pressure B increases. With a pressure equal or greater than atmospheric pressure within the collection chamber 704, milk in the pathway can flow through valve 101 from the collection chamber 704 into the collection container 210, i.e., milk release phase. The barrier 100 utilizes its pre-load during displacement to pneumatically apply a pressure to the milk thus opening the valve 101 and releasing the milk into the collection container 210. As the milk is released, the pressure applied by the barrier 100 decreases to the pre-load represented by the initial state of the barrier. After the milk is released, the valve 101 closes. The vacuum system then repeats the phases again through this cycle, beginning with the suction phase.

It will be noted that the invention may be adapted so that the barrier does not return completely to the initial state. This might be in a situation where minimum vacuum level is to be maintained in the breastshield during pumping. The tendency of the barrier nonetheless causes it to move toward that initial state, if not achieving it.

Figure 10:
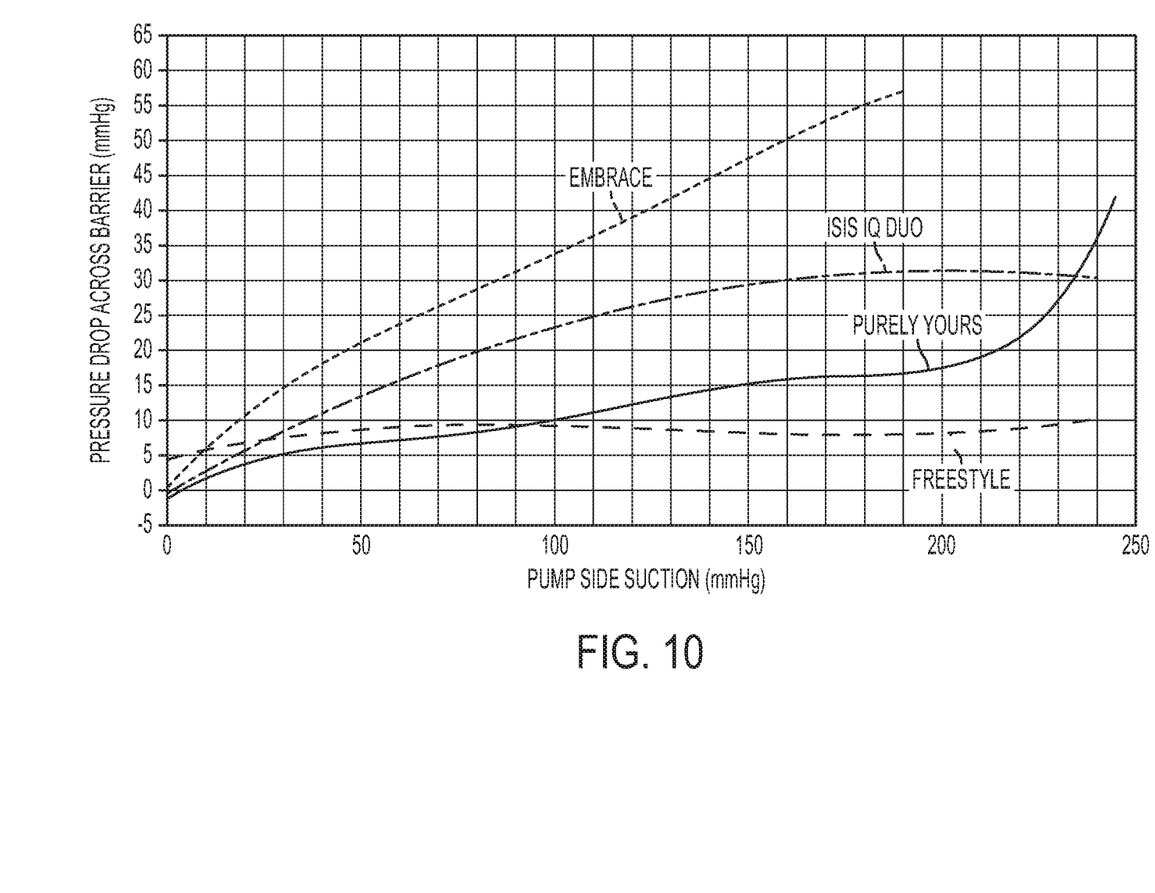
FIG. 10 is a comparison chart of performance (curves) of various membranes.

FIG. 10 is a comparison chart of performance (curves) of various contamination barriers. As indicated in the graph of FIG. 10, pressure drop across the barrier, or differential pressure, is indicated along the y-axis (in millimeters of mercury) and vacuum side suction (in millimeters of mercury) is along the x-axis. The graph indicates values based on one pumping cycle drawn up to −250 mmHg. The pressure drop is the difference between the pressure on the breastshield side of the barrier and the pressure on the pump side of the barrier.

The FREESYTLE curve was made with an embodiment of the invention. As indicated, it had a pre-load of 4 mmHg, i.e., it required that amount of vacuum before the barrier began to move. PURELY YOURS, ISIS IQ DUO and EMBRACE are commercial products. They are assembled without a pre-load. As can by seen in FIG. 10, FREESTYLE, which incorporates the advantages of the present invention, had the most consistent pressure drop across the barrier for the entire vacuum range. This illustrates an excellent mechanical transfer, and a reduced amount of energy required on the breastpump system, when a barrier contemplated by the present invention is implemented. The FREESYTLE barrier is most efficient in that the energy loss is minimal once the pre-load is overcome.

It is understood that there may be many shapes, sizes, and configurations of the barrier that will fall within the scope of the invention. The use of the terms dome, concave and convex does not limit the invention to a round barrier. Any shape, e.g., non-round barrier is contemplated with material thickness and shape varying with respect to distance and angle from the center of the barrier to achieve the spring action discussed herein. It is seen that the objects set forth above, among those made apparent from the preceding description, are efficiently attained and, since certain changes may be made in the above constructions without departing from the spirit and scope of the invention, it is intended that all matter contained in the above description or shown in the accompanying drawings shall be interpreted as illustrative and not in a limiting sense. It is also to be understood that the following claims are intended to cover all of the generic as well as specific features of the invention herein described, and all statements of the scope of the invention that, as a matter of language, might be said to fall therebetween.

While the present invention has been described with reference to a particular embodiment, those skilled in the art will recognize that many changes may be made thereto without departing from the scope of the present invention. Each of these embodiments and variants thereof is contemplated as falling with the scope of the claimed invention, as set forth in the following claims.

What is claimed is:

1. A breastpump assembly, comprising:
a breastshield;
a conduit structure adapted to convey pressure and liquid;
a collection container communicating with the conduit structure;
a housing detachably coupled to the breastshield and the collection container;
a vacuum source communicating with the housing; and
a resilient barrier mounted within the housing between the breastshield and the collection container made of a material providing a spring-like function assembled in a pre-loaded initial state between a breastshield side and a vacuum source side of the housing, in the pre-loaded initial state the resilient barrier has a compressed configuration with a center portion aligned with an intermediate portion of the resilient barrier thereby providing a residual force for the resilient barrier, wherein the intermediate portion comprises a flat surface and substantially surrounds the center portion, wherein the resilient barrier is configured to achieve a distended state, wherein a plane of the center portion and a plane of the intermediate portion are substantially parallel to each other, and the center portion and the intermediate portion are joined via a sidewall, wherein a plane of the sidewall is angular to the plane of the center portion and the plane of the intermediate portion, wherein the angular sidewall is directly coupled to the center portion, and in response to an applied vacuum from the vacuum source and when the applied vacuum is released, the resilient barrier is configured to achieve the pre-loaded initial state.

2. A breastpump assembly, comprising:
a breastshield;
a vacuum source in communication with the breastshield via a vacuum line, a housing having a front side and a back side, the housing being detachably coupled to the breastshield and a collection container; and
a resilient barrier mounted within the housing between the breastshield and the collection container, the resilient barrier being made of a material providing a spring-like function assembled in an initial pre-loaded state between the front side and the back side of the housing, wherein a height of the resilient barrier taken along a central axis from a rim of the resilient barrier to a front surface of a convex side of the resilient barrier in the pre-loaded initial state is less than the height of the resilient barrier in a free distended state, the pre-loaded initial state providing a residual force for the resilient barrier, wherein the resilient barrier is configured to achieve the distended state in response to an applied vacuum from the vacuum source and the resilient barrier is configured to achieve the initial pre-loaded state upon release of the applied vacuum, wherein in the distended state, a plane of a center portion and a plane of an intermediate portion are substantially parallel to each other and joined via an angular sidewall directly coupled to the center portion.

3. A breastpump assembly, comprising:
a contamination barrier located in a pressure line between a pressure generating pump and a breastshield;
a housing having a breastshield side and a pressure side; and
the contamination barrier separates and isolates the breastshield side from the pressure side, the contamination barrier assembled within the housing between the breastshield and a collection container, the contamination barrier being in an initial pre-loaded state between the breastshield side and the pressure side, wherein the contamination barrier has a compressed configuration with a center portion aligned with an intermediate portion of the contamination barrier, positioned between the center portion and a rim of the contamination barrier, wherein the intermediate portion comprises a flat surface and substantially surrounds the center portion, such that the contamination barrier has a pre-set bias in a direction toward the breastshield side of the housing in the absence of a pressure applied by the pressure generating pump, and wherein, the contamination barrier is configured to achieve a distended state wherein a plane of the center portion and a plane of the intermediate portion are substantially parallel to each other and are joined via a sidewall, directly coupled to the center portion.

4. The breastpump assembly of claim 3, wherein the contamination barrier is configured to achieve the distended state in response to an applied pressure from the pressure generating pump, and the contamination barrier returns toward the initial state upon release of the applied pressure.

5. The breastpump assembly of claim 4, wherein the contamination barrier has a generally convex shape and at least in part comprises a convex barrier side, and is assembled within the housing so that the pre-set bias presses the convex barrier side against an internal sidewall surface on the breastshield side of the housing in the initial state.

6. The breastpump assembly of claim 5, wherein the convex barrier side further has at least one undulation formed in its surface generally concentric with a center of the convexity.

7. The breastpump assembly of claim 6, wherein an internal side sidewall of the breastshield of the housing has a shape that generally conforms to that of the convex barrier side, such that the contamination barrier and the breastshield side sidewall substantially mate when in facial engagement.

8. The breastpump assembly of claim 7, wherein the contamination barrier is configured to be inverted in the distended state.

9. The breastpump assembly of claim 8, wherein the housing has a vacuum side sidewall, wherein the vacuum side sidewall of the housing has a shape that generally conforms to that of the contamination barrier in the distended state, such that the contamination barrier and the vacuum side sidewall substantially mate when in facial engagement.

10. The breastpump assembly of claim 6, wherein the contamination barrier has a plurality of generally concentric undulations configured to provide bending moments for the contamination barrier.

11. A breastpump assembly comprising:
a breastshield configured to receive a woman's breast and nipple;
a container for expressed milk coupled to the breastshield;
a source of vacuum;
a vacuum conduit structure configured to convey a vacuum from the source to the breastshield;
a resilient barrier between the breastshield and the container, wherein the resilient barrier is in the vacuum conduit structure located in close proximity to the breastshield, the resilient barrier being mounted within a housing, the housing having a breastshield side and a vacuum side, the resilient barrier separating the breastshield side from the vacuum side, the resilient barrier having an outer surface and an inner surface forming at least in part a convex shape configured such that the resilient barrier has a bias toward the convex shape, wherein, the resilient barrier is configured to achieve a distended position wherein in the distended position, a plane of a center portion and a plane of an intermediate portion are substantially parallel to each other, the intermediate portion, comprising a substantially flat surface and substantially surrounding the center portion, wherein the angular sidewall is directly coupled to the center portion, the housing having a breastshield side internal sidewall that generally conforms to the convex shape on the outer surface of the resilient barrier, the resilient barrier being mounted in the housing such that the convex shape of the resilient barrier is compressed and the bias presses the resilient barrier against the internal sidewall.

12. The breastpump of claim 11, wherein the barrier has at least one undulation formed generally radially spaced from and concentric about the center of the barrier, the breastshield side internal sidewall of the housing having a surface shape that generally matches the barrier convex shape on the outer surface of the barrier such that the barrier substantially mates with the breastshield side internal sidewall surface in facial engagement in the initial pre-load condition.

13. The breastpump of claim 12, wherein the vacuum side includes a rearwall surface having a shape that generally matches a shape of the barrier in the distended position, wherein when the barrier is in the distended position, the deformed barrier substantially mates with the rearwall surface of the vacuum side in facial engagement in the distended state.

14. The breastpump assembly of claim 1, wherein the center portion and the intermediate portion are parallel in separate planes.

* * * * *